(12) United States Patent
Hayden et al.

(10) Patent No.: US 12,194,461 B2
(45) Date of Patent: Jan. 14, 2025

(54) PARTICLE AGGREGATION METHOD AND SYSTEM IN A CHANNEL

(71) Applicant: Technische Universität München, Munich (DE)

(72) Inventors: Oliver Hayden, Moosburg (DE); Rune Barnkob, Munich (DE)

(73) Assignee: Technische Universität München, Munich (DE)

( * ) Notice: Subject to any disclaimer, the term of this patent is extended or adjusted under 35 U.S.C. 154(b) by 939 days.

(21) Appl. No.: 17/287,362

(22) PCT Filed: Oct. 15, 2019

(86) PCT No.: PCT/EP2019/077936
§ 371 (c)(1),
(2) Date: Apr. 21, 2021

(87) PCT Pub. No.: WO2020/083710
PCT Pub. Date: Apr. 30, 2020

(65) Prior Publication Data
US 2021/0387186 A1    Dec. 16, 2021

(30) Foreign Application Priority Data

Oct. 24, 2018 (EP) .................................. 18202362

(51) Int. Cl.
*B01L 3/00* (2006.01)
*G01N 15/00* (2024.01)
*G01N 15/10* (2024.01)

(52) U.S. Cl.
CPC ... *B01L 3/502715* (2013.01); *B01L 3/502761* (2013.01); *G01N 15/10* (2013.01);
(Continued)

(58) Field of Classification Search
CPC ......... B01L 3/502715; B01L 3/502761; B01L 2200/0668; B01L 2300/0663; G01N 15/10; G01N 2015/0092
See application file for complete search history.

(56) References Cited

U.S. PATENT DOCUMENTS

| 730,957 A | 6/1903 | Newell |
|---|---|---|
| 6,216,538 B1 | 4/2001 | Yasuda et al. |

(Continued)

FOREIGN PATENT DOCUMENTS

| WO | WO-93/19367 A2 | 9/1993 |
|---|---|---|
| WO | WO-03/079006 A1 | 9/2003 |
| WO | WO-2017/127120 A1 | 7/2017 |

OTHER PUBLICATIONS

International Search Report and Written Opinion from International Application No. PCT/EP2019/077936 dated Nov. 21, 2019.
(Continued)

*Primary Examiner* — Brian J. Sines
(74) *Attorney, Agent, or Firm* — MARSHALL, GERSTEIN & BORUN LLP

(57) ABSTRACT

A method for aggregating a cluster of particles having a target cluster constitution in a channel comprising a retention section comprises the steps of establishing a fluid stream comprising a fluid carrier medium and particles of at least one type through said channel; controlling a supply of said particles of at least one type into the fluid stream; operating a retention mechanism to aggregate at least part of said particles in an aggregation region within said retention section, to thereby form said cluster of particles; monitoring, while operating said retention mechanism, the particles in at least part of said channel for obtaining a monitoring signal associated with the cluster and/or with the particles moving in the fluid stream; determining a current cluster constitution from the monitoring signal; comparing said current cluster constitution with said target cluster constitution; and controlling at least one of said particle retention mechanism and said supply of said particles of at least one type, such that said current cluster constitution approaches said target cluster constitution.

20 Claims, 10 Drawing Sheets

(52) U.S. Cl.
CPC .................. *B01L 2200/0668* (2013.01); *B01L 2300/0663* (2013.01); *G01N 2015/0092* (2013.01)

(56) References Cited

U.S. PATENT DOCUMENTS

| | | |
|---|---|---|
| 6,929,750 B2 | 8/2005 | Laurell et al. |
| 7,340,957 B2 | 3/2008 | Kaduchak et al. |
| 9,719,065 B2 | 8/2017 | Bazou et al. |
| 2013/0327130 A1 | 12/2013 | Hoyos et al. |
| 2014/0011186 A1 | 1/2014 | Suenaga et al. |
| 2014/0131204 A1 | 5/2014 | Chou et al. |
| 2017/0166860 A1 | 6/2017 | Presz, Jr. et al. |

OTHER PUBLICATIONS

Moshksayan et al., "Spheroids-on-a-chip: Recent advances and design considerations in microfluidic platforms for spheroid formation and culture," Sensors and Actuators, B263:151-176 (2018).

Ohlin et al., "Influence of acoustic streaming on ultrasonic particle manipulation in a 100-well ring-transducer microplate," J. Micromech. Microeng. 23:12 pages (2013).

Polonchuk et al., "Cardiac spheroids as promising in vitro models to study the human heart microenvironment," Scientific Reports, 12 pages (2017).

Wiklund, "Acoustofluidics 12: Biocompatibility and cell viability in microfluidic acoustic resonators," Lap Chip 12:2018-2028 (2012).

PARTICLE AGGREGATION METHOD AND SYSTEM IN A CHANNEL

CROSS-REFERENCE TO RELATED APPLICATIONS

This is a U.S. National Phase of International Application No. PCT/EP2019/077936, filed Oct. 15, 2019, which claims priority to European Application No. 18202362.2, filed Oct. 24, 2018, the contents of which are incorporated herein by reference.

FIELD OF THE INVENTION

The present invention is in the field of particle trapping in microfluidic channels. More precisely, the present invention relates to integrated microfluidic circuits with particle manipulation mechanisms for dynamic cell cluster aggregation.

BACKGROUND

Lab-On-a-Chip (LOC) devices provide microscopic laboratories with integrated microfluidic circuits for pre-defined chemical or biological analysis methods. Microfluidic channels in such a device define fluid pathways for small fluid volumes and allow introduction of fluid media, analytes and probes into the chip.

Traditionally, such LOC-devices provide analysis regions for an input fluid injected into a microfluidic channel, wherein each analysis region can contain a plurality of different probes, such as DNA-sequences, to provide multiplexing of analysis steps traditionally performed in parallel or in sequence. The small size of these systems and the low fluid volumes involved then allow reducing costs, safety measures and amount of probe material and can lead to faster analysis due to parallelization of pre-defined process steps.

The conventional way of using such systems is according to the steps of distributing the analytes among chambers of the microfluidic circuit, optionally followed by incubation, labelling of the analytes, or fixation and subsequent analysis of the resulting analysis target in the chambers after a certain time.

Dual et al. ("Ultrasonic microrobotics in cavities: devices and numerical simulation" Lab Chip, 2012, 12, 4010-4021) describe general principles of two dimensional trapping of spherical particles in cavities of microfluidic systems by shaping a trapping potential induced by ultrasonic excitation. By modulating the acoustic excitation, particles can be rotated as well as transported between defined positions of a microdish.

US 2009/0226994 A1 discloses particle manipulation in a flow channel with acoustic forces applied transverse to the channel compatible with confocal microscopy techniques.

Modulation of the acoustic forces of a plurality of acoustic transducers allows separation and parking of particles in the channel to enrich and partition a particle stream into different chambers.

Olofsson et al. ("Acoustic formation of multicellular tumor spheroids enabling on-chip functional and structural imaging." Lab Chip, 2018, 18(16): 2466-2476) describe in vitro culturing of multicellular tumor spheroids in a microchip. To address imaging and analysis issues, an ultrasonic standing wave (USW) based culture platform for parallel formation, staining and imaging of 100 whole multicellular tumor spheroids is proposed, wherein acoustic forces define two-dimensional aggregation regions for cells in a microdish. A protein coating is employed to delimit the spheroids and to prevent attachment to the walls of the microdish. The formation of the tumor cell aggregates after different times of incubation can be imaged using microscopy of the microdish.

U.S. Pat. No. 6,216,538 discloses a particle manipulation device with a plurality of acoustic transducers arranged in an array to define a two dimensional array of trapping locations for particles. By selectively driving the plurality of transducers, the particles can be controllably moved and brought to an overlap to induce controlled cell fusion.

U.S. Pat. No. 9,719,065 B2 discloses formation of a plurality of cell aggregates in several acoustic nodes by submitting a fluid stream to acoustic forces for a predetermined period, incubating the aggregates trapped in the pressure node and allowing settling of the aggregates on top of each other in the absence of acoustic excitation via the control of gravitational forces.

SUMMARY OF THE INVENTION

The known methods and corresponding devices however suffer either from low control over the aggregation process or from long aggregation times due to complex control schemes, such that the composition of aggregates is either randomized or the aggregates become distorted by the manipulation. Thus, close to in vivo cell clusters have remained difficult to simulate.

In particular, trapping arrays with dynamic control and acoustic single cell tweezers for full positional control lead to long cell aggregation times and high control complexity while at the same time posing limits on fluid streams in the system, such that particles inadvertently adhere to walls of the channel. At the same time, the often high particle trapping forces are assumed to be associated with distorted cell behavior and thereby reduce comparability with in vivo studies. Non-dynamic arrays lead to cell aggregates with randomized composition and structure.

The object of the invention is therefore to provide a simple manipulation method and a corresponding system which allows providing a custom aggregate of cells and adjusting the composition and matrix elements of the cell aggregate to provide a research and analysis platform for medical and biological studies with well-defined starting conditions, low invasiveness and repeatable experimental specifics.

This object is solved by a method and an aggregating system for aggregating a cluster of particles according to the independent claims. The dependent claims relate to preferred embodiments.

According to a first aspect, the invention relates to a method for aggregating a cluster of particles having a target cluster constitution in a channel comprising a retention section. The method comprises the steps of establishing a fluid stream through said channel, said fluid stream comprising a fluid carrier medium and particles of at least one type; and controlling a supply of said particles of at least one type into the fluid stream. The method further comprises operating a retention mechanism to aggregate at least part of said particles in an aggregation region within said retention section, to thereby form said cluster of particles; and monitoring, while operating said retention mechanism, the particles in at least part of said channel for obtaining a monitoring signal associated with the cluster and/or with the particles moving in the fluid stream. Further, the method comprises determining a current cluster constitution from the monitoring signal; comparing said current cluster constitution with said target cluster constitution; and controlling at least one of said particle retention mechanism and said supply of said particles of at least one type, such that said current cluster constitution approaches said target cluster constitution.

Thus, by dynamically inferring said current cluster constitution from said monitoring signal a feedback loop can be implemented to dynamically control cluster aggregation from said fluid stream containing said particles of at least one type through operation of one or both of the supply of said particles of at least one type and the retention mechanism. The resulting cluster having the target cluster constitution can then be used for repeatable studies with well-defined initial conditions.

The cluster constitution can correspond to a synopsis or a selection of determined and observable properties of the cluster of particles retained in the retention section of the channel, wherein the current cluster constitution relates to a dynamic evaluation of the cluster constitution based on the monitoring signal, which should be evaluated during the aggregation of the cluster. Preferably, the cluster constitution comprises a dynamic evaluation of the cluster structure and composition, wherein a composition should be understood to comprise single-particle resolved information, such as the number of particles of a certain type aggregated in the cluster, or information relating to such single-particle resolved information with a pre-determined uncertainty level.

For example, the cluster constitution may comprise information on a cluster volume or a cluster size in at least one dimension, preferably in two or three dimensions, such that the number of particles of the certain type aggregated in the cluster can be determined from the cluster constitution with an uncertainty on the number of particles of the certain type smaller than 50%, in particular smaller than 30%, preferably smaller than 20%. However, most preferably, the cluster constitution relates to a dynamic evaluation of the cluster structure and composition based on the monitoring signal, wherein said composition is derived from a tracking of said particles of at least one type in the channel and the cluster constitution relates to single-particle resolved information, comprising an aggregation history of said particles in the channel, such that said composition comprises information on the particle number as well as on the particle type retained in the cluster.

Based on the cluster constitution, the particle retention mechanism or the supply of particles of the at least one type can be controlled to modify the aggregation probability of particles in the fluid stream and/or to modify a current concentration of said particles of at least one type in the fluid stream, such that the current cluster constitution approaches the target cluster constitution and a cluster with a predetermined cluster constitution can be reliably formed.

In a preferred embodiment, the cluster constitution comprises information on at least one of: a size of the cluster, a composition of the cluster, a structure of the cluster, a shape of the cluster and an orientation of the cluster.

The particles referred to herein are objects having a different optical and/or mechanical property from the surrounding fluid carrier medium, such as to allow monitoring and retention of said particles within the channel. Preferably, the particles have a density deviating from the density of the fluid carrier medium by less than 50%, preferably by less than 30%, such as to facilitate controlled retention of the particles in the channel in the presence of gravitational forces. The particles can correspond to cells, micro particles, multi-cell objects, such as cell aggregates or multi-cell organisms, fluid droplets or polymer structures, combinations thereof, or the like. Accordingly, the cluster corresponds to a two- or three-dimensional body aggregated from said particles.

In a preferred embodiment, the particles of at least one type are cells of at least one type or are formed by cells of at least one type and the cluster relates to a cluster of cells.

The trapping of cells can be of particular interest for medical and biological analysis, and the fluid environment in the channel can promote isolated trapping and incubation of said cluster of cells. Said cells can, when retained in said retention region, form a cell cluster with inter-cell links, such that a linked cell cluster may be obtained for the aggregation of a pre-defined cluster for a specific analysis. Said linked cell cluster may behave similar to a single large particle.

The cells may be retained by a plurality of retention mechanisms, such as magnetic, electrostatic, acoustic, optic and/or hydrodynamic mechanisms. However, to limit distortion and interference with natural cell behavior, acoustic and hydrodynamic retention mechanisms are preferably employed for providing the main retention mechanism for retaining said cells of at least one type in the retention region.

In a preferred embodiment, operating the retention mechanism comprises generating an acoustic field in the retention section.

Acoustic waves can modulate a pressure profile in the fluid stream through said channel, which can induce directional forces on particles having a mass density and/or compressibility different from the fluid carrier medium forming the fluid stream. Furthermore, the acoustic pressure can act on fluids of different mass densities, such as for manipulating particles enclosed in a fluid droplet with a different mass density than the surrounding fluid. A difference of the mass density and/or compressibility between the carrier medium and the particle can allow energy transfer between acoustic waves and the particle via scattering of acoustic waves on the particle to thereby induce a directional force onto the particle. The fluid carrier medium may be a cell culture medium for said cells. By superimposing a plurality of acoustic waves, such as counter-propagating acoustic waves and/or surface acoustic waves, or by forming acoustic cavities in the channel, a retention region may be defined for said cells by acoustic forces or by a combination of acoustic forces and hydrodynamic forces.

In a preferred embodiment, operating the retention mechanism comprises generating an acoustic standing wave in the retention section, the standing wave having a pressure node or a pressure anti-node in the aggregation region.

In particular, the channel may form an acoustic cavity in the retention section, wherein said acoustic cavity is associated with a pressure node or a pressure anti-node in the aggregation region when excited with an acoustic excitation from the retention mechanism having a certain frequency. Most preferably, said certain frequencies are chosen to provide a pressure node or a pressure anti-node in a defined subspace of the acoustic cavity for defining the aggregation region. For example, said certain frequencies may correspond to a resonant frequency of said acoustic cavity for obtaining a single or multiple pressure nodes and nodal surfaces.

Even though the following description will mostly refer to the example of a single pressure node, the skilled person will appreciate that a plurality of pressure nodes can be excited in the retention section to define the aggregation region, and that "a pressure node" can therefore be seen as equivalent to "one or more pressure nodes". Furthermore, a plurality of acoustic waves may overlap to define one or more pressure nodes along one or more spatial dimensions, or in other words, a "node" of an acoustic wave generally relates to a "nodal surface" in space. A superposition of acoustic waves along different spatial directions can then induce a nodal line or a nodal focus point in space to define the aggregation region. For example, in cuboid, cylindrical or ellipsoid cavities, standing acoustic waves along different spatial dimensions may be individually excited to define a focus region for said particles of at least one type in a certain location of the cuboid, cylinder or ellipsoid.

In some embodiments, the acoustic cavity is substantially symmetric along two or three dimensions to facilitate generating the pressure node in the aggregation region. For example, in the case of a circular/spherical cavity, a single excitation frequency can be used to generate a nodal line/point in the center or the circular/spherical cavity, when the excitation frequency matches a resonant frequency of the circular/spherical cavity. In other embodiments, the shape of the acoustic cavity is non-symmetric, such as to facilitate dynamically adjusting the retention force on the cluster along different spatial dimensions.

Additionally, both pressure nodes and pressure anti-nodes may be used for aggregating a cluster of particles, based on whether the particles are acoustically hard or acoustically soft with respect to the acoustic properties (mass density and/or compressibility) of the surrounding fluid carrier medium. However, for the sake of brevity, the following description will focus mostly on pressure nodes.

In some embodiments, the acoustic cavity in the channel is formed by a widening of the channel in a lateral direction of the channel, for example a circular, elliptic, or polygonal widening of the channel, for localizing said aggregation region in said widening. Hydrodynamic drag forces on said particles of at least one type may be reduced in said widening, while fluid streams around said aggregation region in the widening of the channel may prevent particle attachment onto channel walls. Thus, a simplified device with structurally favored trapping conditions may be provided.

Preferably the method comprises applying a vertical retention force to guide said particles of at least one type through said channel away from a bottom or top wall of said channel.

In some embodiments, said acoustic cavity is a three dimensional cavity for providing a three dimensional trapping potential. For example, the acoustic cavity may also comprise a widening in the vertical direction to provide a vertical acoustic cavity mode for generating a selected particle retention force in the aggregation region along the vertical direction.

In some embodiments, said acoustic cavity is arranged at an offset from a main fluid stream direction outside the retention section, such as at an offset from an outlet of the retention section for the fluid stream, to thereby promote the escape of gas bubbles from the retention section due to gravitational forces.

In a preferred embodiment, controlling said retention mechanism comprises adjusting a retention strength of the retention mechanism, in particular based on a size of the cluster determined from the monitoring signal.

Acoustic forces can depend on a size of the particle. During said aggregating of said particles of at least one type, the size of the cluster should increase, such that a pressure induced by said retention mechanism onto the particles in the cluster may increase. By adjusting said retention strength of the retention mechanism based on said current cluster constitution, a constant or nearly constant force on said particles in said cluster can be obtained while the cluster can remain retained in the aggregation region.

In some embodiments, the particles of at least one type are cells of at least one type or are formed by cells of at least one type and the cluster relates to a cluster of cells, and the retention strength of the retention mechanism based on acoustic forces is adapted based on the current cluster constitution of the cluster, such that a force on said cells in said cluster of cells does not increase linearly with the size of the cluster.

Adapting the acoustic pressure on the cluster of cells based on the current cluster constitution can reduce distortion of the cell behavior by the retention mechanism.

In a preferred embodiment, controlling said supply of said particles of at least one type comprises adjusting the concentration of said particles of at least one type in said fluid stream based on the current cluster constitution determined from the monitoring signal.

The fluid stream may be a laminar fluid stream to guide the particles through the channel. Additionally, the supply of particles can be at least partially controlled by selectively guiding the particles in the channel using acoustic forces. In some embodiments, the flow of said fluid stream may be controlled to adjust the supply of particles of at least one type into the retention section. Moreover, the supply of particles of at least one type may be adjusted by controlling a particle stream controllably injected into the fluid stream via a separate inlet of the channel to independently control the flow of the fluid stream and the supply of said particles of at least one type.

For example, said supply of said particles of at least one type may be stopped when the current cluster constitution approaches the target cluster constitution, for example when said current cluster constitution is equal to said target cluster constitution or deviates from said target cluster constitution by a predefined threshold, such as deviating from said target cluster constitution by a certain particle number or size, such as by less than 1, 2, 3 or more particles or by less than 30%, in particular by less than 20%, preferably by less than 10% of a particle number, volume or size specified by the target cluster constitution.

In a preferred embodiment, said particles of at least one type comprise a first type of particles and a second type of particles and the method further comprises controlling a supply of the first type of particles and of the second type of particles into the fluid stream, such that said current cluster constitution approaches said target cluster constitution.

The dynamic control over the cluster of particles based on the monitored current cluster constitution may allow forming particle clusters with a target composition and structure for aggregating predefined mixed particle type clusters in the aggregating region. Controlling the supply of particles of the first and second type into the fluid stream can provide a simple control scheme for aggregating complex cluster structures.

In a preferred embodiment, said target cluster constitution comprises one or both of a target composition and a target structure and in particular a cluster constitution relating to a mixed particle type aggregate or to a core/shell aggregate with a target composition.

A particle concentration in the fluid stream may then be controlled based on the current cluster constitution to obtain a cluster with predefined structure and composition.

The current cluster constitution for the dynamic control of the supply or particle retention mechanism can be determined from the monitoring signal associated with the cluster and/or with the particles moving in the fluid stream.

In a preferred embodiment, the monitoring signal represents at least one or both of a position and a velocity of one or more particles of said particles of at least one type.

In some embodiments, the monitoring signal comprises information on a size or a volume of said cluster.

In principle, a variety of different monitoring devices are generally suitable for providing said monitoring signal. For example, a capacitive/magnetic measurement of the channel may be used to infer a particle presence or particle size in the channel based on a capacitive/magnetic property of said particle. Additionally, an acoustic resistance of said fluid stream may be monitored to obtain said monitoring signal and a series of monitoring signals may be generated through photoacoustic imaging to track a property of a particle or the cluster.

In preferred embodiments, however, said monitoring signal is an optical signal, in particular a microscope image or a series of microscope images of said particles moving in the fluid stream or arranged in said cluster. The particles may then feature an optical property different from the surrounding carrier medium to allow identifying said particles in the monitoring signal. In some embodiments, said microscope images of the channel are obtained with at least one of standard microscopy, Raman imaging and digital holographic microscopy.

The series of microscope images can allow tracking the particles moving in the fluid stream and thereby allow inferring from said movement of said particles whether said particles attach to or pass said cluster. Thus, a current cluster constitution of said cluster can be derived from particle tracking information of particles moving in the fluid stream, wherein the current cluster constitution can be determined with single-particle accuracy. Additionally, said optical signal may allow direct determination of the size of said cluster. Combining the information on the cluster and on the particle tracking based on the monitoring signal, an accuracy in the determination of the current cluster constitution can be increased.

In some embodiments, the monitoring signal is used to study inter-particle interactions by adjusting the particle retention force of the retention mechanism on the cluster based on the current cluster constitution and monitoring an association or a dissociation of the particles in the cluster.

In some embodiments, the dynamic position relates to tracking information on a monitored particle determined from the microscope image or from a series of microscope images captured by a camera, wherein the tracking information is determined from the microscope image, preferably using particle tracking velocimetry. Said optical signal for a particle tracking velocimetry can be obtained by a combination of a camera and a microscope, which should be configured to record a microscope image or a series of microscope images of said particles moving in the fluid stream or aggregated in said cluster. When said particles of at least one type are cells of at least one type, said cells of at least one type are preferably not labeled and said optical signal should be label-free to reduce distortion of natural cell behavior.

In a preferred embodiment, the cluster constitution comprises a number of particles in the cluster, wherein the number of particles is determined from at least one of a tracking history of a plurality of said particles of at least one type in said channel and from the size of the cluster in the retention section. For example, the number of particles of a certain type can be obtained by a difference between particles entering the retention section and particles leaving the retention section. In some examples, the particle history retains information on an observed attachment between said particles of at least one type and the cluster based on the monitoring signal.

Further, said optical signal may allow dynamic control over the aggregation of said particles of at least one type in the fluid stream.

In a preferred embodiment, the method further comprises determining, from said monitoring signal, whether one or more particles of at least one type move into or are about to move into said retention section and controlling said retention mechanism, in particular adjusting a retention strength of said retention mechanism, based on said current cluster constitution, for selectively directing said one or more particles to said cluster or for avoiding that said one or more particles reach said cluster.

In particular, in the case of a retention mechanism based on acoustic forces, a force required for retaining a cluster comprising a plurality of particles of said at least one type in said aggregation region can be lower than a force required for retaining a single particle of said at least one type in said aggregation region. Thus, selective aggregation of said one or more particles can be implemented with a dynamic modulation of said retention strength.

In some embodiments, the retention mechanism may control the flow of the fluid stream and the selective aggregation of said one or more particles is implemented by controlling a relative retention strength of the retention mechanism. Since the particles are retained in the retention section against a fluidic drag force imparted onto the particles of at least one type by the fluid stream, a relative retention strength can be controlled by controlling a flow of the fluid stream. Thus, the retention mechanism may control one or both of the flow of the fluid stream and the acoustic wave amplitude for controlling the retention strength of the retention mechanism.

In some embodiments, said retention mechanism may selectively avoid that said one or more particles reach said cluster by exciting said retention section with a second acoustic frequency, said second acoustic frequency being different from an acoustic frequency for retaining said cluster in said aggregating region, to thereby guide at least a predominant part of said one or more particles to pass around said cluster.

Selective control over the aggregation of particles can allow for faster aggregation times, since a concentration of said particles of at least one type in said fluid stream can be increased, and an aggregation of particles still dissolved in said fluid stream upstream the retention section can be avoided when said current cluster constitution approaches said target constitution, such as when a target number of particles of a certain type aggregated in said cluster has been reached.

In a preferred embodiment, the method further comprises identifying the type of one or more particles of said particles of at least one type moving in said channel based on the monitoring signal, in particular based on the position and velocity of said one or more particles determined from the monitoring signal.

In some embodiments, the type of particle can be derived from the monitoring signal such as by a particle-type specific optical contrast or from the particle path. For example, when particles of different types are injected via different inlets, a particle type may be registered and tracked for a monitored particle when said monitored particle enters the channel leading into the retention section.

Additionally, based on a known functional relationship of particle size and retention force based on acoustic waves, a size of said particles of at least one type may be determined from a tracking history of said particle in the channel. Different types of particles usually have different sizes or at least different acoustic contrast (difference in mass density and compressibility between the particle and the surrounding fluid medium), such that based on the speed of the particles in the channel, different types of particles moving in the channel can be determined. Based on the determined particle type in a dilute stream of particles of at least one type, a dynamic particle path can be imposed onto said particles of a certain type by adjusting the retention strength of the retention mechanism, wherein said dynamic particle path selectively approaches the aggregation region or passes said aggregation region in the channel. Thus, dynamic selective aggregation from a fluid stream containing more than one type of particles can be performed based on the monitoring signal.

In a preferred embodiment, the method further comprises adapting at least one of a pH, an ion concentration, an oxygen concentration and a nutrient concentration in the fluid stream based on the current cluster constitution determined from the monitoring signal. Adapting the oxygen and/or the nutrient concentration based on the current cluster constitution may allow adjusting the oxygen and/or the nutrition concentration based on a size of the cluster, such as for adapting the oxygen and/or the nutrient concentration for said size of the cluster or for selectively creating a given physiological environment for said cell cluster, such as nutrient or oxygen stress, signaling molecules, bispecific antibodies or the like.

In a preferred embodiment, the method further comprises adapting a matrix material concentration in the fluid stream based on the current cluster constitution determined from the monitoring signal. Said matrix material may e.g. modify a structure of a cell cluster, may induce inter-cell links or may provide an extracellular matrix for said cells. Controlling said concentration of matrix material may thereby allow approaching a target cluster constitution, such as a target cluster constitution comprising a target inter-cell link structure or a target cluster constitution corresponding to core/shell cell clusters. In some embodiments, the method comprises triggering a crosslinking of the matrix material based on the cluster constitution by applying an optical trigger to the matrix material in the aggregation region. The triggering the crosslinking of the matrix material may allow embedding aggregated particles or covalently attaching matrix materials on the particle surface.

In some embodiments, the method further comprises controlling a concentration of therapeutic biological material in the fluid stream based on the current cluster constitution, wherein said therapeutic biological material may correspond to signaling molecules, antibodies, biosimilars, T-cells, monocytes, macrophages, or the like. For example, the therapeutic material concentration in the fluid stream can be increased when the current cluster constitution reaches a cluster constitution threshold to perform inter-cell interaction studies in a given physiological environment.

In a preferred embodiment, the method further comprises providing a particle retention force in said channel outside of the retention section for preventing aggregating of said particles on walls of said channel. For example, said particle retention force may comprise a retention force keeping particles in suspension and guiding said particles of at least one type in the center of said channel into said retention section. The inlet section may have a cylindrical shape to avoid distortion of the trapping potential by air bubbles with acoustic modes having a pressure node or a pressure antinode in the center of the channel.

In a second aspect, the invention relates to an aggregating system for aggregating a cluster of particles having a target cluster constitution in a channel. The aggregating system comprises a fluid guiding section comprising said channel, said channel comprising a retention section, a fluid control mechanism, a retention mechanism associated with said channel, a monitoring device and a control device. The fluid control mechanism is configured to establish a fluid stream through said channel, said fluid stream comprising a fluid carrier medium and particles of at least one type and to control a supply of said particles of at least one type into the fluid stream. The retention mechanism is configured to aggregate at least part of said particles in an aggregation region within said retention section of said channel, to thereby form said cluster of particles. The monitoring device is configured for monitoring the particles in at least part of said channel to provide a monitoring signal associated with the cluster and/or with the particles moving in the fluid stream. The control device is configured to operate said retention mechanism and said fluid control mechanism and to receive a monitoring signal from the monitoring device while operating said retention mechanism. The control device is further configured to determine a current cluster constitution from the monitoring signal, to compare said current cluster constitution with said target cluster constitution and to control at least one of said particle retention mechanism and said supply of said particles of at least one type, such that said current cluster constitution approaches said target cluster constitution.

In some embodiments, the control device and/or the fluid control mechanism implement any one of the embodiments of the method according to the first aspect.

The control device may be any controller suitable for receiving said monitoring signal and/or for operating said retention mechanism or fluid control mechanism, such as a microprocessor, an FPGA, an ASIC, a computer or the like, wherein the control device is configured to receive said monitoring signal and to implement said retention mechanism or said fluid control mechanism or to send operating parameters to said retention mechanism or to said fluid control mechanism.

The channel in said fluid guiding section of the aggregating system is preferably a microfluidic channel etched into a fluid retaining material, such as a silicon or silicon oxide based material slab. The fluid retaining material preferably comprises monitoring windows with an at least partially transparent material for optically monitoring said particles in said part of said channel to provide the monitoring signal associated with the cluster and/or with the particles moving in the fluid stream.

The channel can comprise one or more inlets for operatively connecting said fluid control mechanism to the channel. The fluid control mechanism can establish said fluid stream through the channel from said one or more inlets through the retention section to an outlet of the channel by the use of fluid pumps, such as syringe pumps or peristaltic pumps.

In a preferred embodiment, the cluster constitution comprises information on at least one of: a size of the cluster, a composition of the cluster, a structure of the cluster, a shape of the cluster and an orientation of the cluster.

In a preferred embodiment, the particles of at least one type are cells of at least one type or are formed by cells of at least one type and the cluster relates to a cluster of cells.

Preferably, the control device is configured to control the temperature of a fluid environment in the retention section for the cluster of cells within a margin around an optimal incubation temperature, such as a temperature deviating from 37° C. by less than 2° C., preferably by less than 1° C. For example, the control device may control a temperature of the fluid medium in the retention section by controlling a temperature of the fluid stream introduced into the channel. In some embodiments, the control device is configured to control a heater and/or a cooling device operatively coupled to the channel.

In a preferred embodiment, the retention mechanism comprises an acoustic wave generator operatively coupled with the retention section and configured to generate an acoustic field in the retention section, wherein the acoustic wave generator is in particular configured to generate a standing wave having a pressure node or a pressure anti-node in the aggregation region.

In some embodiments, the retention mechanism comprises a surface acoustic wave generator configured to induce a propagating surface acoustic wave in the retention section, in particular at least two surface acoustic wave generators configured to induce at least partially counter-propagating surface acoustic waves.

In some embodiments, the channel comprises an acoustic cavity in the retention section and the retention mechanism comprises an acoustic excitation means for exciting an acoustic wave in the retention section, wherein the acoustic wave in the retention section is in particular a standing wave comprising a pressure node or a pressure anti-node in the aggregation region.

For example, the retention section may correspond to a widening of the channel forming an acoustic cavity, wherein the retention mechanism comprises an acoustic transducer, operatively coupled to said retention section, such as an electrode coupled to a piezoelectric material or a piezoelectric material stack, an IDT operatively coupled with the channel, a combination thereof or the like, for exciting an acoustic standing wave or surface acoustic wave in said retention section.

In a preferred embodiment, said control device is configured to adjust a retention strength of the retention mechanism, in particular based on a size of the cluster determined from the monitoring signal.

In some embodiments, said control device is configured to adjust an amplitude or a frequency of a radiofrequency excitation on said acoustic transducer for controlling the retention strength of the retention mechanism on said particles of at least one type in the retention section.

In a preferred embodiment, the control device is configured to control said supply of said particles of at least one type by adjusting the concentration of said particles of at least one type in said fluid stream based on the current cluster constitution determined from the monitoring signal.

In a preferred embodiment, said monitoring signal represents one or both of a position and a velocity of one or more particles of said particles of at least one type.

In a preferred embodiment, said monitoring signal is an optical signal, wherein said monitoring device preferably comprises a camera and a microscope and is configured to record a microscope image or a series of microscope images of said particles moving in the fluid stream or aggregated in said cluster.

In a preferred embodiment, the control device is configured to determine, from said monitoring signal, whether one or more particles of at least one type move into or are about to move into said retention section and to control said retention mechanism, in particular to adjust a retention strength of said retention mechanism, based on said current cluster constitution, for selectively directing said one or more particles to said cluster or for avoiding that said one or more particles reach said cluster.

In a preferred embodiment, the cluster constitution comprises a number of particles in the cluster and the control device is configured for determining the number of particles from one or both of a tracking history of a plurality of said particles of at least one type in said channel and the size of the cluster in the retention section.

In a preferred embodiment, the control device is further configured to identify the type of one or more particles of said particles of at least one type moving in said channel based on the velocity of said one or more particles determined from the monitoring signal.

In a preferred embodiment, said particles of at least one type comprise a first type of particles and a second type of particles and the method further comprises controlling a supply of the first type of particles and of the second type of particles into the fluid stream, such that said current cluster constitution approaches said target cluster constitution.

In some embodiments, the channel comprises separate inlets for the first type of particles and for the second type of particles to independently introduce the first type of particles and the second type of particles into the fluid stream in the fluid guiding section close to the retention section.

In some embodiments, the channel comprises one inlet for introducing the fluid stream and at least two additional inlets for mixing the fluid stream in a mixing section of the channel with a first stream and a second stream comprising the first and second type of particles, respectively. Providing said two additional inlets and controlling the concentration of the first and second type of particles with said two additional inlets can reduce a flow distance from said mixing section to the retention section and thereby increase an aggregation speed for said cluster with compositional control of said cluster.

In a preferred embodiment, said target cluster constitution comprises one or both of a target composition and a target structure, in particular a cluster constitution relating to a mixed particle type aggregate or to a core/shell aggregate with a target composition.

A core/shell aggregate comprises a core region in the center of the aggregate and a shell region around said core region, wherein at least one of a particle type, particle concentration, matrix structure and density of particles in the core region is different from the shell region. For example, a core/shell aggregate may comprise a core region in the center of the core/shell aggregate having a given concentration of particles of a first type and a shell region having a different concentration of said particles of the first type. Preferably, a core/shell aggregate further comprises particles of a second type, wherein a concentration of particles of the second type in the core region is different from the concentration of particles of the second type in the shell region, such as a core/shell aggregate comprising predominantly particles of the first type in the core region and comprising predominantly particles of the second type in the shell region. Core/shell aggregates can simulate specific biological aggregates or can provide shielding of the particles in the inner core region of the aggregates from outer influences by the particles in the shell region, for example during aggregate transfer.

In a preferred embodiment, the control device is further configured to adapt at least one of a pH, an ion concentration, an oxygen concentration and a nutrient concentration in the fluid stream based on the current cluster constitution determined from the monitoring signal.

In a preferred embodiment, the control device is further configured to adapt a matrix material concentration in the fluid stream based on the current cluster constitution determined from the monitoring signal.

In a preferred embodiment, the system is further configured to provide a particle retention force in said channel outside of the retention section for preventing aggregating of said particles on walls of said channel.

In a third aspect, the invention relates to a computer program comprising machine readable instructions which when executed by a processor cause the processor to control an aggregating system for aggregating a cluster of particles in a channel by implementing a method according to an embodiment of the first aspect or to control an aggregating system according to an embodiment of the second aspect.

DETAILED DESCRIPTION OF EMBODIMENTS

The features and numerous advantages of the method and system according to the present invention will best be understood from a detailed description of preferred embodiments with reference to the accompanying drawings, in which.

Figure 1:
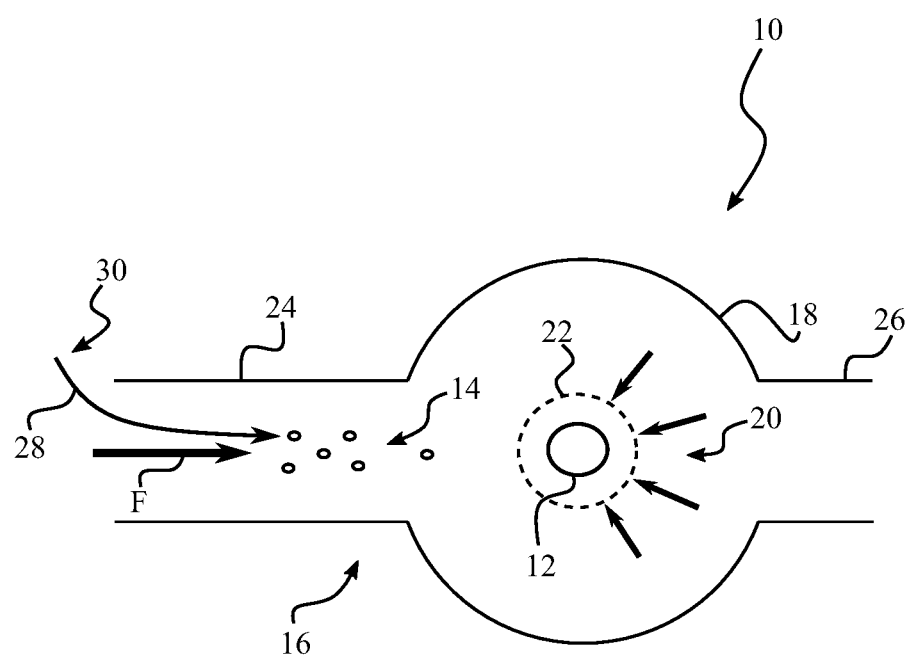
FIG. 1 is a schematic illustration of an aggregating system for aggregating a cluster of particles according to an example.

FIG. 1 shows an aggregating system 10 for aggregating a cluster 12 of particles 14 of at least one type in a channel 16 according to an example. The channel 16 comprises a retention section 18 operatively coupled to a retention mechanism 20 to aggregate said particles 14 in an aggregation region 22 to thereby form said cluster 12 of particles 14. A fluid stream F flows from an inlet section 24 through the retention section 18 towards an outlet section 26 of the channel 16 and transports said particles 14 of at least one type through said channel 16. The concentration of said particles 14 of at least one type in the fluid stream F is controlled by controlling a first stream 28 of particles 14 injected into the channel 16 from a supply 30.

The retention mechanism 20 is only symbolically represented in FIG. 1 (but explicitly illustrated in FIGS. 3, 4, 6, and 8-10B) by straight solid black arrows in the retaining section 18 indicating a retaining force on the particles 14 in the retention section 18, wherein the retaining force of said retention mechanism 20 on the particles 14 should be selected to be greater than a fluidic drag force on the particles 14 by the fluid stream F. Preferably, said retaining force should further provide a lateral force component at an angle to the direction of the fluid stream F, such that an aggregation region can be defined for aggregating the cluster 12 of particles 14.

A supply 30 of particles 14 of at least one type and the fluid stream F can be controlled to provide a selected concentration of particles 14 of at least one type moving in the fluid stream F towards the retention section 18. When entering the retention section 18, the retention force of the retention mechanism 20 may then define or establish a preferential particle path towards the aggregation region 22. Thus, by supplying the particles 14 into the retention section 18 and by providing a retention force above a certain threshold determined by the flow of the fluid stream F, the particles 14 can aggregate in the aggregation region 22 thereby forming the cluster 12.

In the prior art, a supply 30 of particles 14 is simply initiated and then stopped after a certain time, thereby forming a cluster 12 with randomized composition and structure, since the particles 14 arrive in the aggregation region 22 at in principle non-deterministic arrival times and may not attach to the cluster 12 with certainty.

Figure 2:
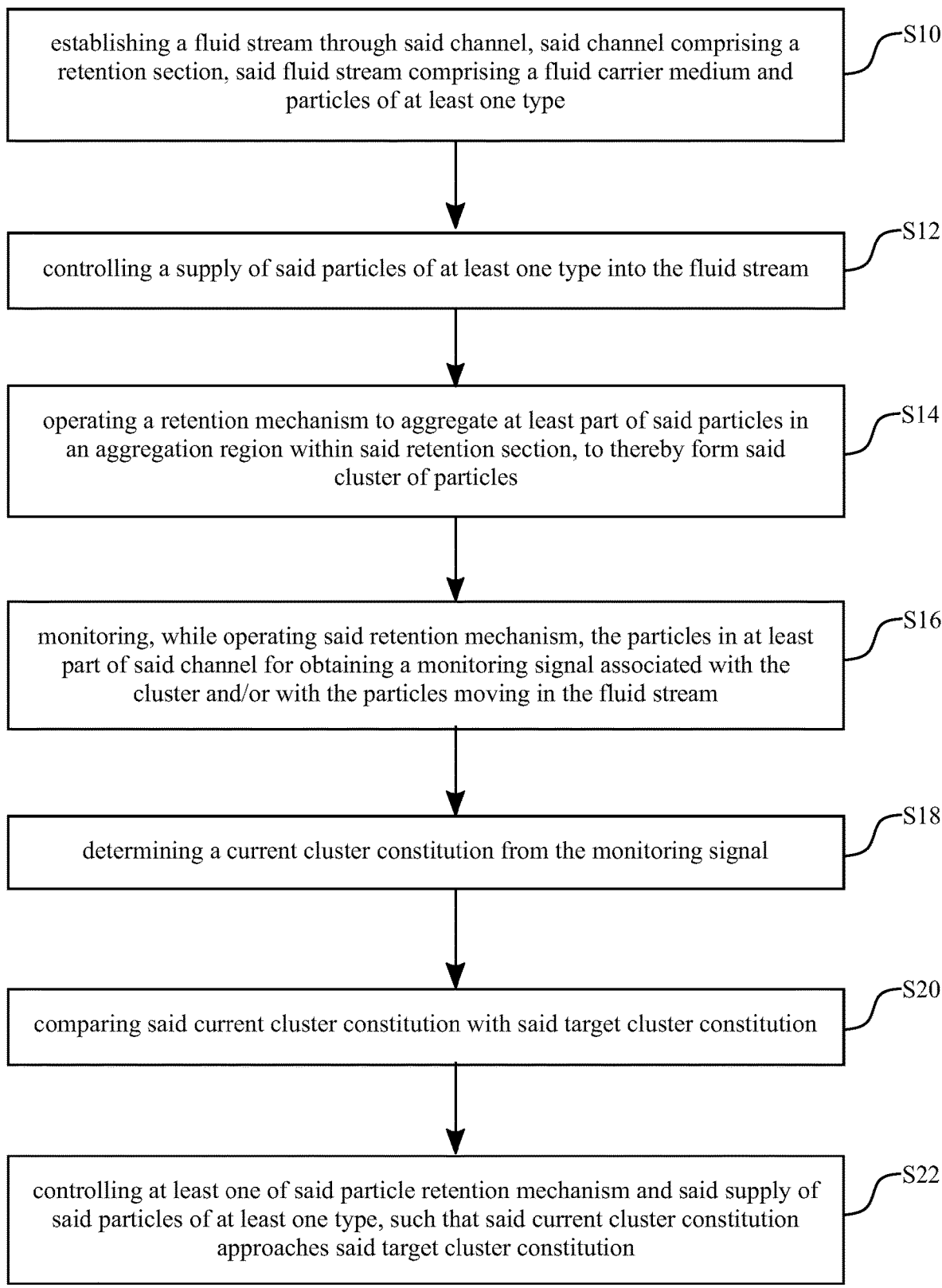
FIG. 2 illustrates a flow diagram illustrating method steps for aggregating a cluster of particles according to an example.

FIG. 2 illustrates a method for aggregating the cluster 12 of particles 14 having a target cluster constitution in the channel 16. The method comprises the steps of establishing the fluid stream F through said channel 16, said channel 16 comprising the retention section 18, said fluid stream F comprising a fluid carrier medium and particles 14 of at least one type (step S10) and controlling a supply of said particles 14 of at least one type into the fluid stream F (step S12). The method further comprises operating a retention mechanism 20 to aggregate at least part of said particles 14 in an aggregation region 22 within said retention 18 section, to thereby form said cluster 12 of particles 14 (step S14) and monitoring, while operating said retention mechanism 20, the particles 14 in at least part of said channel 16 for obtaining a monitoring signal associated with the cluster 12 and/or with the particles 14 moving in the fluid stream F (step S16). Further, the method comprises determining a current cluster constitution from the monitoring signal (step S18), comparing said current cluster constitution with said target cluster constitution (step S20) and controlling at least one of said particle retention mechanism 20 and said supply 30 of said particles 14 of at least one type, such that said current cluster constitution approaches said target cluster constitution (step S22).

Figure 3:
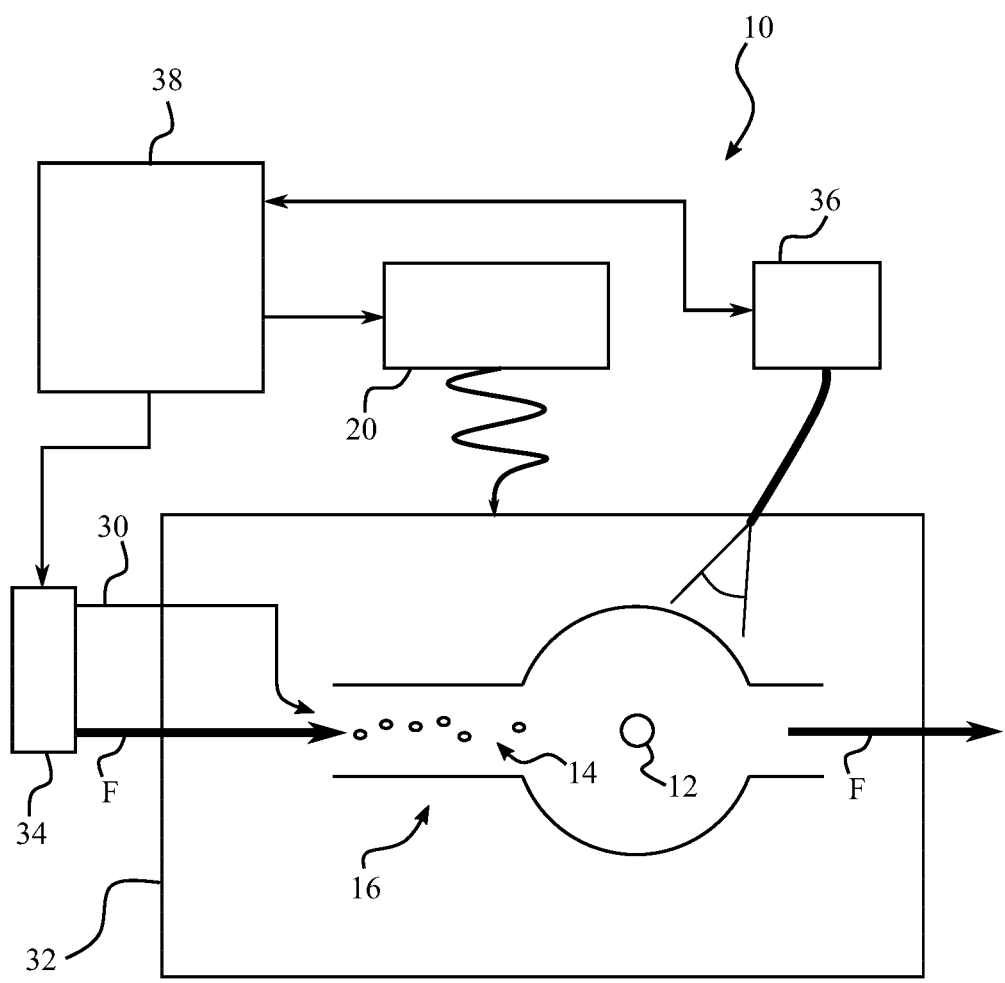
FIG. 3 is a schematic illustration of an aggregating system for aggregating a cluster of particles according to another example.

FIG. 3 illustrates a schematic diagram of an example of an aggregating system 10 for implementing said method. The aggregating system 10 comprises a fluid guiding section 32, a fluid control mechanism 34, a monitoring device 36 and a control device 38. The fluid guiding section 32 comprises the channel 16 and is implemented in a microfluidic environment, such as a quartz crystal, wherein the channel 16 is etched into the quartz crystal to define a fluid path through the fluid guiding section 32 for the fluid stream F. However, the material for the fluid guiding section 32 can be freely selected from a range of materials compatible with microfabrication technology and being at least partially impervious to the fluid carrier medium, such as silicon, silicon oxide, glass, polymers, such as PDMS or polystyrene, metals, a combination thereof, such as a stacked structure, or the like. Preferably, the material is at least partially transparent in sections of the fluid guiding section 32 for allowing monitoring the cluster 12 with an optical monitoring device 36.

The fluid control mechanism 34 can establish said fluid stream F through said channel 16 by injecting a fluid carrier medium into said fluid guiding section 32. Further, the fluid control mechanism 34 can control a supply 30 of said particles 14 of at least one type into the fluid stream F, such as by injecting a fluid stream F having a selected concentration of said particles 14 into said fluid guide section 32 via the same or different inlets of the fluid guide section 32.

The monitoring device 36 is configured for monitoring at least part of said channel 16 and for providing a monitoring signal associated with the cluster 12 and/or with the particles 14 moving in the fluid stream F. Preferably, the monitoring device 36 is an optical monitoring device, as indicated in the illustration, and typically comprises a microscope and a camera and the fluid guiding section 32 provides monitoring windows in the channel 16 fabricated from an at least partially optically transparent material, such that the cluster 12 and/or the particles in the fluid stream F can be monitored using said combination of a microscope and a camera. The monitoring signal can be a series of microscope images, i.e. a "video stream", which can be provided to the control device 38 at a sufficient rate to track the cluster 12 retained in the retention section 18 and/or the particles 14 moving in the fluid stream F.

The control device 38 of the aggregating system 10 is configured to control the fluid control mechanism 34, the particle retention mechanism 20 and to receive the monitoring signal from the monitoring device 36.

For aggregating the cluster 12 of particles 14 having a target constitution, the control device 38 preferably determines a current cluster constitution of the cluster 12 from the monitoring signal associated with particles 14 moving in the fluid stream F. In particular, the control device 38 should determine the positions of said particles 14 moving in the fluid stream F in real time to track an aggregation process of said particles 14. For example, the monitoring device 36 can provide one or more cameras for providing a stream of camera images for allowing two- or three-dimensional particle tracking velocimetry by the control device 38.

The control device 38 may then determine whether a particle 14 in the fluid stream F aggregates in the aggregation region 22 from the monitoring signal provided by the monitoring device 36. For example, the control device 38 may monitor whether said particle 14 enters said aggregation region 22 and whether said particles 14 leaves said aggregation region 22. When a particle 14 enters and does not leave the aggregation region 22, the control device 38 may determine that said particle has aggregated in the aggregation region 22 and that said particle 14 may now form part of the cluster 12.

Thus, the control device 38 may update the current cluster constitution of the cluster 12 based on the monitoring signal with an updated number of particles 14 aggregated in the cluster 12. The update of the current cluster constitution may be verified or supplemented by a monitoring signal associated with the cluster 12, for example by a size of the cluster 12 in at least one dimension, such as a two-dimensional footprint of the cluster 12 in the monitoring signal or a three-dimensional volume of the cluster determined from the monitoring signal. Additionally, a shape of the cluster 12 may be determined from the monitoring signal.

Based on the size of the cluster 12, the control device 38 may adjust the retention force of the retention mechanism 20 to dynamically control the induced pressure onto the cluster 12 or the aggregation probability for particles 14 in the fluid stream F.

When the current cluster constitution determined from the monitoring signal approaches the predefined target cluster constitution, the control device 38 can control either one of or both of the particle retention mechanism 20 and the fluid control mechanism 34 to conclude aggregating the cluster 12 having the target constitution.

For example, a concentration of the particles 14 in the fluid stream F may be adjusted based on the current cluster constitution to approach said target cluster constitution. A supply 30 of the particles 14 may be stopped when the current cluster constitution as determined from the monitoring signal reaches the target cluster constitution or deviates from the cluster constitution by a given threshold, such that the current cluster constitution can approach said target cluster constitution with a remaining number of particles 14 moving in the fluid stream F upstream of the retention section 18 determined from the monitoring signal.

Additionally, an aggregation probability of particles 14 in the aggregation region 22 may be dynamically controlled with the retention mechanism 20 based on the current cluster constitution.

Figure 4A:
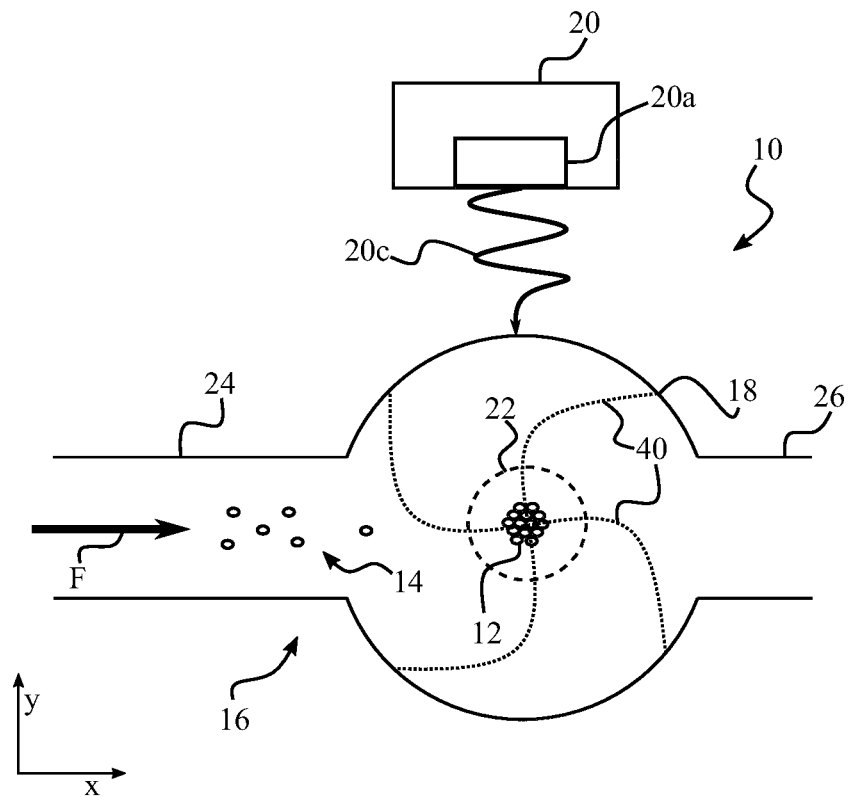
FIG. 4A illustrates a top view of an aggregating system for aggregating a cluster of particles using acoustic standing waves according to an example.
Figure 4B:
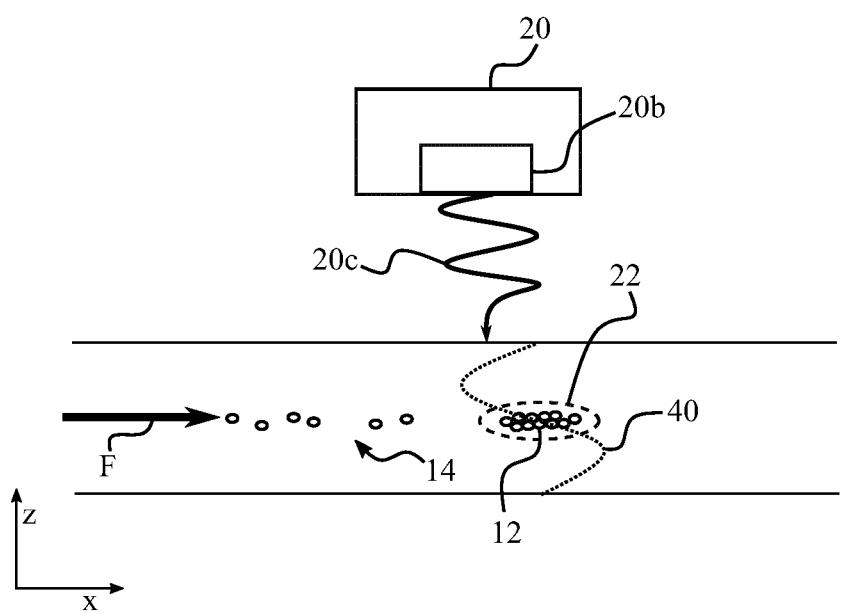
FIG. 4B illustrates a side view of an aggregating system for aggregating a cluster of particles using acoustic standing waves according to an example.

FIG. 4A illustrates a top view along the z-direction onto the x- and y-direction of a preferred embodiment of the aggregating system 10 with a retention mechanism 20 based on acoustic waves. FIG. 4B illustrates a corresponding side view oriented along the y-direction onto the x- and z-direction of the fluid stream F of the same aggregating system 10. In the aggregating system 10 illustrated in FIGS. 4A and 4B, the retention mechanism 20 comprises an acoustic transducer 20a, 20b operatively coupled by the coupling means 20c to the retention section 18 of the channel 16 to thereby form a trapping potential 40 for particles 14 of at least one type in the fluid stream F. The coupling means 20c may be a suitable rigid material portion of the channel 16 for transmitting an acoustic wave excited by the acoustic transducer 20a, 20b to the retention section 18.

In FIGS. 4A and 4B, the retention mechanism 20 and the acoustic transducers 20a, 20b are only schematically shown and are not intended to imply any limitation on the arrangement and shape of the retention mechanism 20 and the acoustic transducers 20a, 20b. Rather, the skilled person will appreciate that a variety of shapes and arrangements of acoustic transducers 20a, 20b can be chosen for inducing an acoustic excitation in the retention section 18 (such as the acoustic transducers 50, 50*a-c* illustrated in FIG. 10A or 10B). Additionally, it will be appreciated that the trapping potential 40 is only schematically represented and its shape may significantly differ from the illustrated profile, for example depending on the specific shape of the retention section 18 or the excitation parameters of the retention mechanism 20. Furthermore, a plurality of aggregation regions 22 may be induced by the retention mechanism 20, said aggregation regions 22 having shapes different from a circular region and having (time-dependent) locations outside of the center position of the retention section 18, depending on the shape of the channel 16, the specifics and parameters of the retention mechanism 20, or the fluidic drag forces in the channel 16. Thus, the illustrated example of a single aggregation region 22 arranged in the static center position of the retention section 18 may only be realized in specific embodiments and should not be construed as limiting for embodiments of the invention.

According to the top view of the channel 16 in FIG. 4A, the channel 16 comprises a roughly circular widening along the lateral y-direction of the channel for providing a two-dimensional acoustic cavity. When the retention mechanism 20 excites the acoustic transducer 20*a* operatively coupled to the retention section 18 with a frequency corresponding to a lateral mode of the acoustic cavity, an acoustic standing wave in the x- and y-direction of the channel 16 may be excited in the fluid carrier medium.

A trapping potential 40 induced in the retention section 18 according to FIG. 4A is illustrated by two perpendicular acoustic pressure profiles depicted in dotted lines induced by a resonant standing acoustic wave, wherein the trapping potential 40 comprises a pressure node in the aggregation region 22, such that a retention force onto a particle 14 in the fluid stream F having a different mass density and/or a different compressibility than the fluid carrier medium is directed towards the center of the aggregation region 22. Thus, the particle 14 entering the retention section 18 is preferentially directed towards the center of the aggregation region 22 to thereby form the cluster 12.

As illustrated in FIG. 4B, the particle retention mechanism 20 may further excite a vertical mode in the channel by operating a second acoustic transducer 20*b* to induce a vertical component of the trapping potential 40, to thereby control a position of said particles 14 in the vertical z-direction. Said vertical mode may correspond to the same or a different acoustic frequency than the lateral mode, and may be excited and adjusted independently of said lateral mode. Naturally, said lateral mode for providing a lateral trapping potential 40 may itself correspond to a plurality of modes and may be excited with a plurality of excitation frequencies. Similarly, the vertical and lateral cavities may share a common resonance frequency and may be collectively excited. However, for the sake of brevity, a detailed description of mode profiles along different directions of the retention section 18 will be largely omitted in the following.

A retention mechanism 20 based on acoustic standing waves may be particularly suitable for biological material, since an interference of the acoustic standing waves with the characteristic behavior of cells can be low. Additionally, a retention force induced by said acoustic standing waves onto the cluster 12 and the particles 14 moving in the fluid stream F can be proportional to a size of the cluster 12 or of the particles 14, such that retaining a cluster 12 may require a lower acoustic pressure force than retaining a single particle 14.

Thus, after an initial forming of the cluster 12, a modulation or dynamic adaption of the amplitude of the acoustic excitation by the retention mechanism 20 can allow dynamic control over particle aggregation in the retention section 18.

Figure 5:
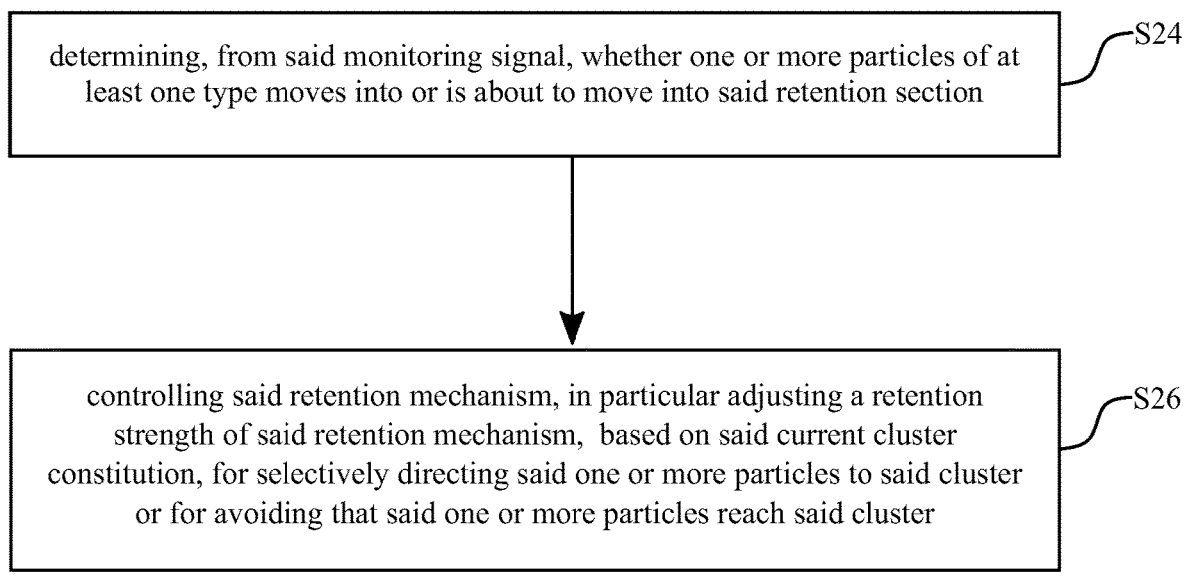
FIG. 5 illustrates a flow diagram for selectively aggregating particles according to an example.

FIG. 5 illustrates an exemplary flow diagram of a method for implementing said dynamic control over particle aggregation by controlling a retention strength of a retention mechanism 20 based on acoustic standing waves. The illustrated method comprises determining, from said monitoring signal, whether one or more particles 14 of at least one type moves into or is about to move into said retention section 18 (step S24) and controlling said retention mechanism 20, in particular adjusting a retention strength of said retention mechanism 20, based on said current cluster constitution, for selectively directing said one or more particles 14 to said cluster 12 or for avoiding that said one or more particles 14 reach said cluster 12 (step S26).

Figure 6:
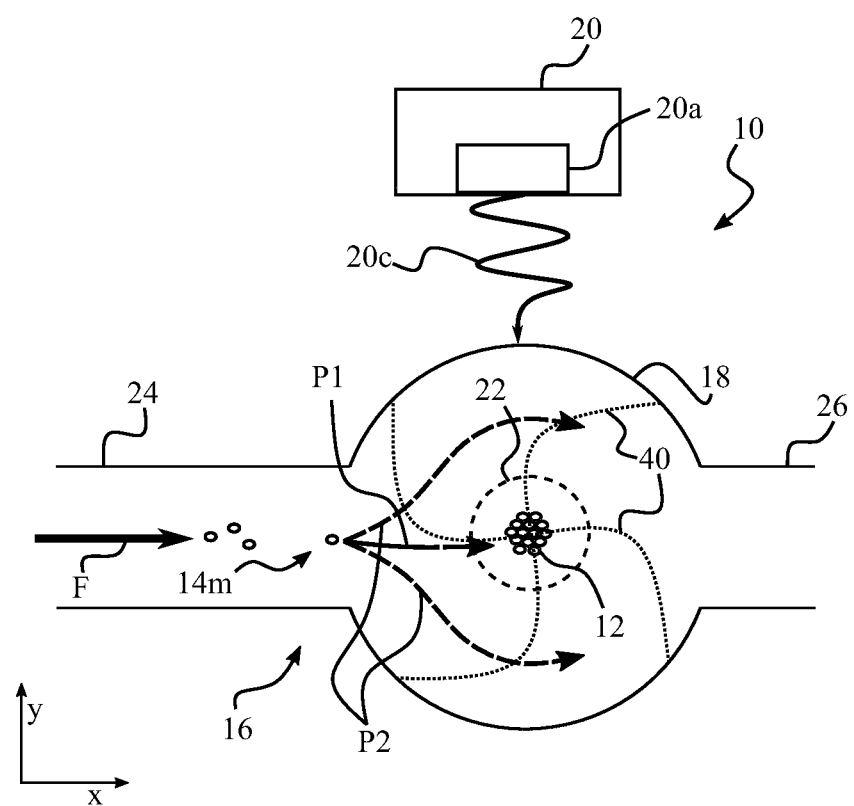
FIG. 6 illustrates a top view of an aggregating system for selectively aggregating a cluster of particles using acoustic standing waves according to an example.

FIG. 6 shows exemplary dynamic particle paths P1, P2 corresponding to the method of FIG. 5 in an illustrated aggregating system 10 according to an example. When the control device 38 determines that a monitored particle 14*m* enters or is about to enter the retention section 18, the retention strength of said retention mechanism 20 can be selectively adjusted to control an estimated particle path of the monitored particle 14*m*.

In the case of a high retention strength of the trapping potential 40, the acoustic forces on the monitored particle 14*m* can overcome fluidic forces on the monitored particle 14*m*, such that said monitored particle 14*m* can be directed into the aggregation region 22 along an aggregation path P1.

In the case of a low retention strength of the trapping potential 40, the acoustic forces induced in the retention section 18 can still retain the cluster 12 having a larger size than the monitored particle 14*m* in the aggregation region 22. However, at the same time the acoustic forces on the monitored particle 14*m* can be lower than the fluidic drag forces on the monitored particle 14*m*. Thus, a fluidic drag around the cluster 12 can transport said monitored particle 14*m* towards the outlet section 26 along a passing path P2 and can thus selectively prevent aggregation of said monitored particle 14*m*.

Figure 7:
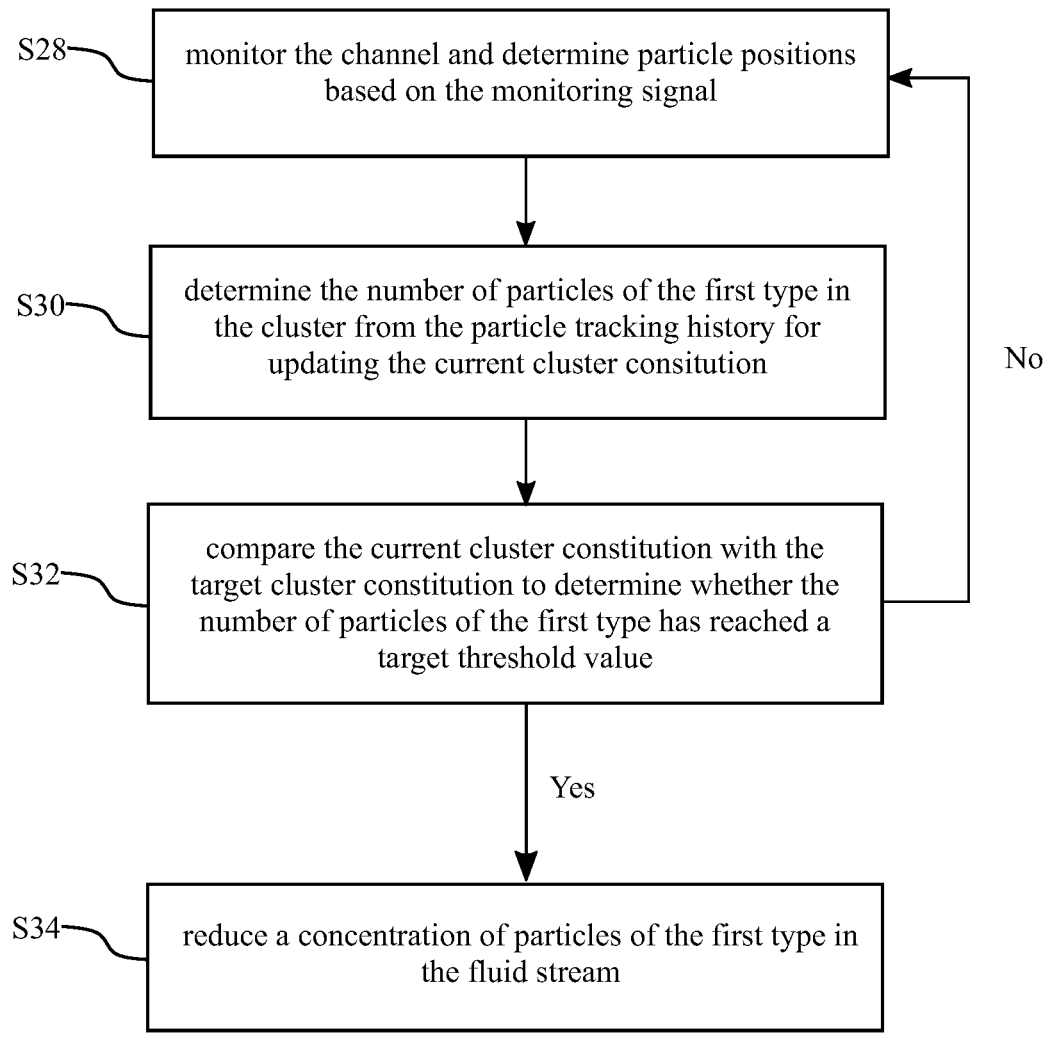
FIG. 7 illustrates a flow diagram illustrating a process of dynamically approaching a target cluster constitution according to an example.

FIG. 7 illustrates an example of a flow diagram for dynamically controlling the cluster composition based on control of a fluid control mechanism 34. In the example of FIG. 7, the control device 38 is configured to monitor the channel 16 by receiving a monitoring signal from the monitoring device 36 and to determine particle positions of particles 14 moving in the fluid stream F based on the monitoring signal (step S28). From a series of determined particle positions, the control device 38 derives a particle tracking history, said particle tracking history comprising a history of particle positions for a plurality of monitored particles 14. The control device 38 determines a number of particles 14 of a first type of particles in the cluster 12 from said particle tracking history and updates the current cluster constitution based on the particle tracking history (step S3*o*).

The control device 38 then compares the current cluster constitution with the target cluster constitution to determine whether the number of particles of the first type has reached a target threshold value, which may be a target value for the number of particles of the first type in the cluster 12 or may deviate from said target value for the number of particles of the first type by a given deviation threshold (step S32).

If the target threshold value has not been reached, the control device 38 continues to monitor the channel 16 (step S28).

If the target threshold value has been reached, the control device 38 can operate the fluid control mechanism 34 to reduce the concentration of particles 14 of the first type in the fluid stream F (step S34), such as to conclude the cluster formation process or to conclude a part of the cluster formation process.

Thus, a cluster 12 with a target number of particles of a certain type can be formed based on the dynamic feedback from the monitoring device 36 configured to track particles 14 moving in the fluid stream F.

Figure 8:
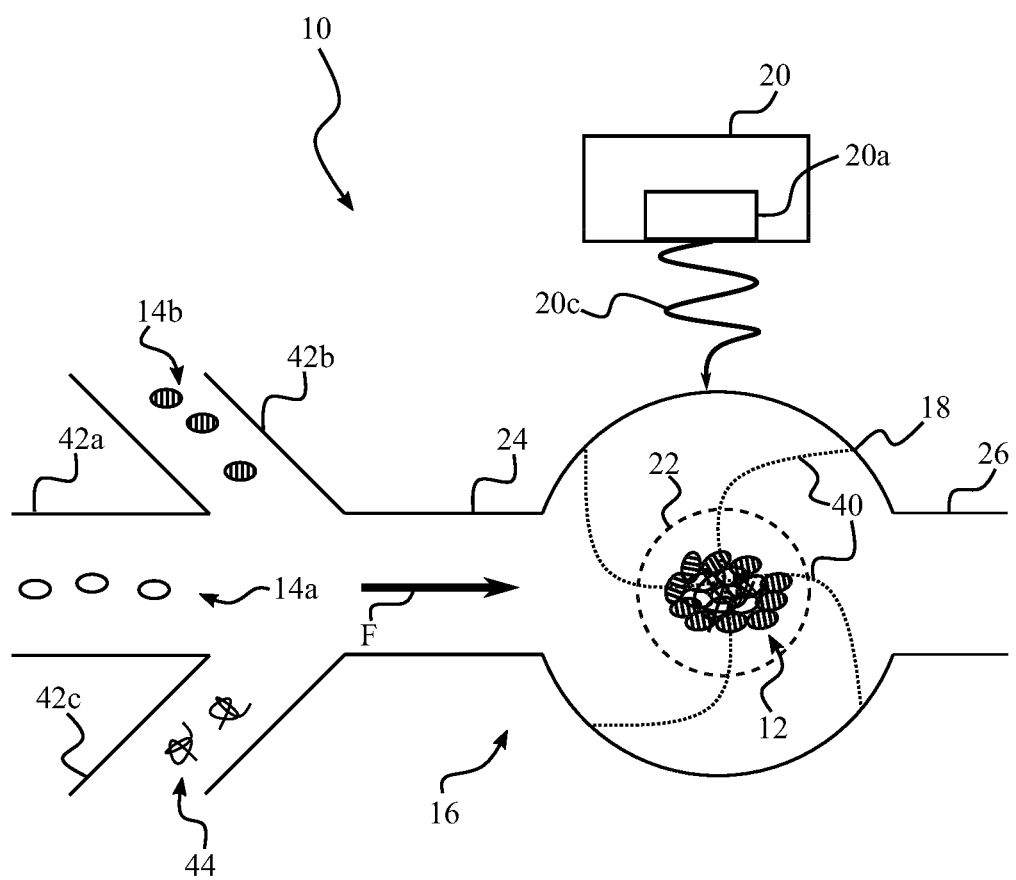
FIG. 8 is a schematic illustration of an aggregating system for aggregating a cluster of several different particles according to an example.

FIG. 8 illustrates a system 10 for aggregating a cluster 12 having a target cluster constitution with a plurality of cluster constituents according to an example. The channel 16 comprises a first inlet 42a for providing a supply of particles of a first type 14a, a second inlet 42b for providing a supply of particles of a second type 14b and a third inlet 42c for providing matrix material 44. The fluid stream F carries the particles of the first type 14a, the particles of the second type 14b and the matrix material 44 towards the aggregation region 22 induced by a trapping potential 40 generated by an acoustic standing wave.

The control device 38 of the system 10 may then induce the formation of a cluster 12 corresponding to a mixed type particle aggregate in the aggregation region 22 by selectively controlling the supply of particles of the first type 14a, of the particles of the second type 14b and/or of the matrix material 44 into the retention region 18 of the channel 16.

For example, when the target constitution is a core/shell aggregate of particles of the first type 14a and particles of the second type 14b as illustrated in FIG. 8, the control device 38 may first control the supply of the first particles 14a to aggregate in a cluster 12 of particles of the first type 14a in the aggregation region 22 corresponding to the core of the cluster 12 to be eventually formed or, in other words, the cluster 12 having the "target constitution". From a monitoring signal of the channel 16 the control device 38 can determine the current cluster constitution including the number of particles of the first type 14a aggregated in the cluster 12. When the number of particles of the first type 14a reaches a threshold value given by the target cluster constitution, a supply of particles of the first type 14a can be stopped.

The control device 38 of the system 10 may control a supply of matrix material 44 through the third inlet 42c to promote aggregation or induce assembly of a matrix structure for the cluster 12 of particles of the first type 14a based on the target cluster constitution. For example, the control device 38 may supply matrix material 44 during or after aggregating the cluster 12 and may adapt a concentration of matrix material 44 based on the current cluster constitution to form a target cluster having a predefined matrix structure of matrix material 44.

Since the matrix material 44 may be weakly affected by the retention force of the retention mechanism 20, dynamic control of the supply of matrix material 44 into the channel 16 based on the current cluster constitution may limit an accumulation of matrix material 44 in the fluid guiding section 32 and in the channel 16, such that the system 10 may be re-used more often or with lower downtimes.

In some examples, the matrix material 44 may be optically activated and the control device 38 may induce selective chemical activation of the matrix material 44 by controlling an optical excitation of the channel 16 in the retention section 18 based on the current cluster constitution.

Following an aggregation of the cluster 12 of particles of the first type 14a with or without a supply of matrix material 44 into the retention section 18 of the channel 16, the control device 38 may control a supply of particles of the second type 14b into the channel 16 to form a shell portion of the cluster to be eventually formed. The particles of the second type 14b may then be transported by the fluid stream F into the aggregation region 22 to thereby form a mixed type particle aggregate, such as a core/shell aggregate as illustrated in FIG. 8.

Thus, dynamic control based on the current cluster constitution can allow forming clusters 12 having a target cluster constitution, wherein the cluster constitution can specify structure and composition of the cluster 12 including a composition of the cluster 12 based on particle type and matrix material distribution.

In some examples, the control device 38 controls the retention strength of the retention mechanism 20 to selectively direct particles 14a, 14b of a certain type into the aggregation region 22 based on the current cluster constitution, for example by performing the method according to FIG. 5 for particles of said certain type. The type of particle may be determined from particle tracking velocimetry of the particles along the channel 16 from the first inlet 42a or from the second inlet 42b. In some examples, the control device 38 identifies the type of the particle 14a, 14b from a velocity of the particles 14a, 14b in an acoustic field, such as an acoustic field in the retention section 18.

A mixed type particle aggregate can allow studying cell migration as well as allow producing target cell structures for specific biological or medical studies. The cluster 12 having the target cluster constitution can also be removed from the channel 16 and inserted into an animal model (e.g. mouse) for comparative studies.

Furthermore, the cell aggregation process can be controlled and studied in real time, wherein, when a particle of the second type 14b enters the aggregation region 22 or is within a pre-determined distance from the cluster 12, the fluid stream F may be dynamically stopped and a retention force of the retention mechanism 20 may be reduced as compared to a previous flow value to allow for simulating aggregation of said particle of the second type 14b in the absence of the fluid stream F or in the absence of an outer stimulus.

In some examples, the current cluster constitution determined from the monitoring signal comprises the orientation of the cluster 12 and the system 10 controls the aggregation of particles 14 based on the orientation of the cluster 12.

For example, the system 10 may selectively direct a particle towards the cluster 12 when an orientation of the cluster is such that an aggregation of said particle 14 along a calculated or estimated trajectory for said particle 14 approaches the current cluster constitution and the target cluster constitution. The current cluster constitution may approach the target cluster constitution when the particle 14a, 14b is direct towards an intended location for the particle 14a, 14b according to a target cluster structure and composition. In the case of a core/shell-structure, the system 10 may selectively direct particles of the second type 14b towards positions roughly equally distributed around the circumference of the cluster 12.

In some examples, the system 10 controls the orientation of the cluster 12 by operating the retention mechanism 20, such that the current cluster constitution approaches the target cluster constitution.

To control the orientation of the cluster 12, the retention mechanism 20 may modulate an amplitude, a frequency and/or a phase of the acoustic waves, or may induce a strain on the channel 16 along a certain direction to modulate the trapping potential 40, such that the trapping potential 40 induces a torque on the cluster 12.

Figure 9:
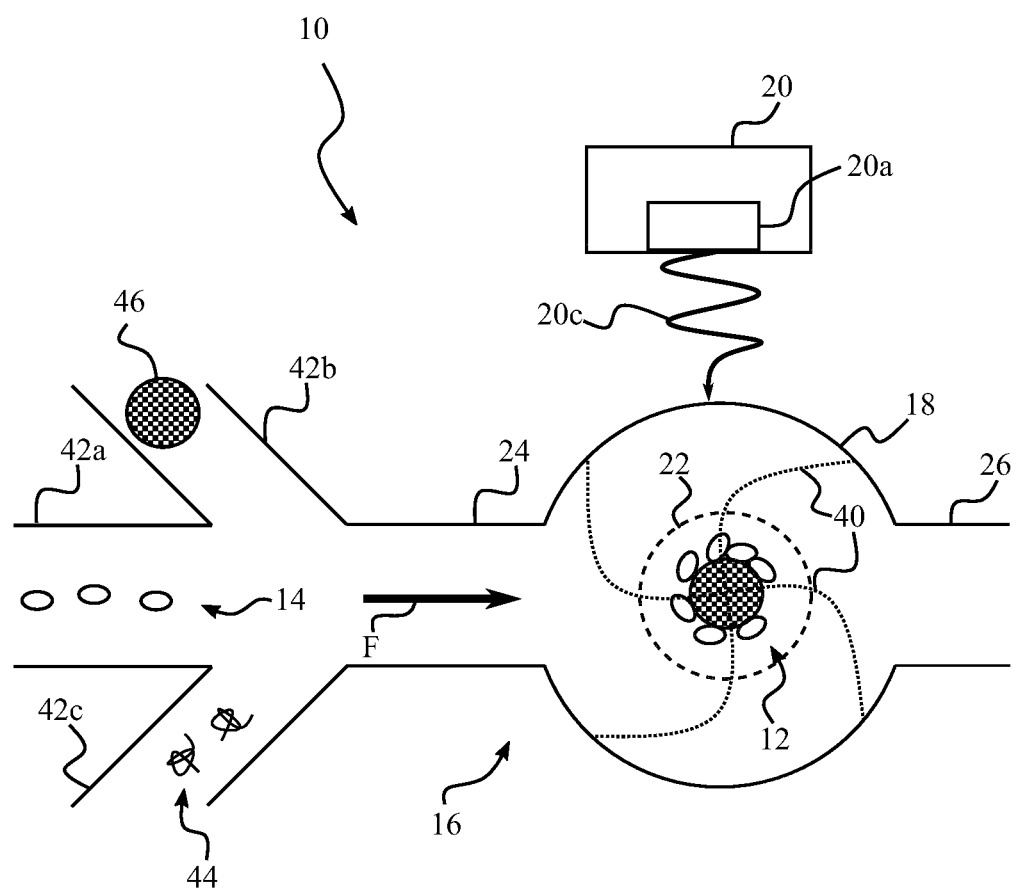
FIG. 9 is a schematic illustration of an aggregating system for aggregating a cluster of particles around a large object according to an example.

FIG. 9 illustrates a system 10 for studying stepwise interaction between cell type particles 14 and a large trapped object 46 having a mass density and/or compressibility different from the fluid carrier medium, wherein the channel 16 comprises a second inlet 42b for providing a supply of a large object 46, such as a bead.

The control device 38 may control the fluid control mechanism 34 to direct the large object 46 into the retention section 18. When the control device 38 determines that the large object 46 enters or is about to enter the retention section 18, the control device 38 may stop a supply of large objects 46. When the control device 38 determines that the large object 46 is trapped in the retention section 18, the control device 38 may update the current cluster constitution with the presence of the large trapped object 46 in the retention section 18.

The control device 38 may then control the supply 30 of the particles 14 and/or the retention mechanism 20, to selectively direct particles 14 into the aggregation region 22 for stepwise interaction with the large trapped object 46, wherein a retention force can be increased to direct a particle 14 towards the large trapped object 46. As in the example illustrated in FIG. 8 a distribution of the particles 14 on the surface of the large trapped object 46 can be selectively controlled via the retention mechanism 20.

In some examples, the retention force is reduced when the particle 14 enters the aggregation region 22 or is within a predetermined distance from the cluster 12 as determined from the monitoring signal to reduce an effect of an outer stimulus on the aggregation.

Figure 10A:
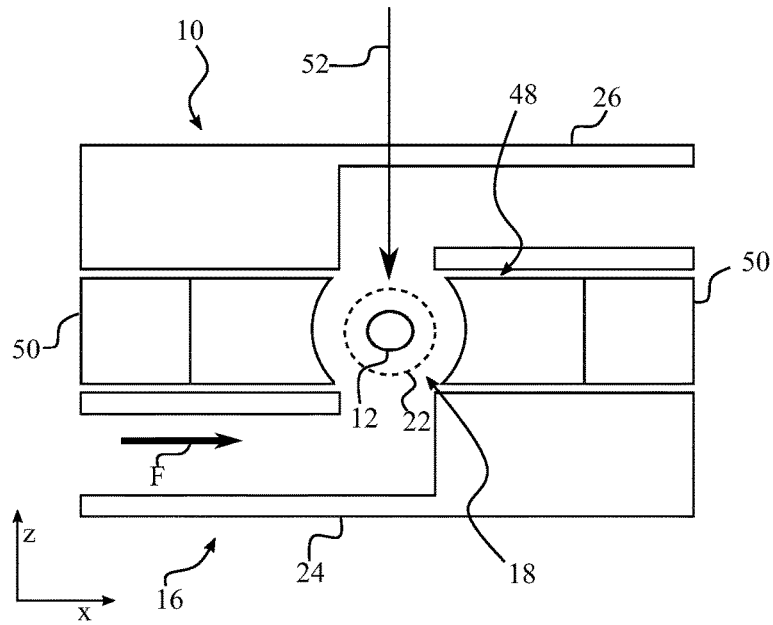
FIG. 10A is a schematic illustration of an aggregating system for aggregating a three-dimensional cluster of particles according to an example.
Figure 10B:
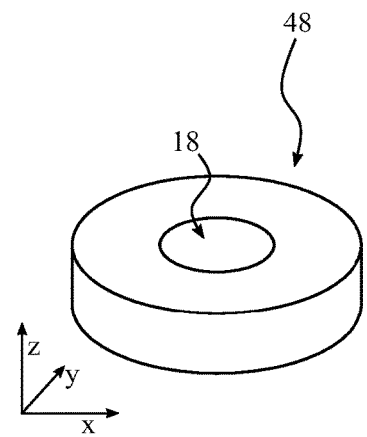
FIG. 10B is a perspective view of an acoustic lens employed in the example of FIG. 10A.
Figure 10C:
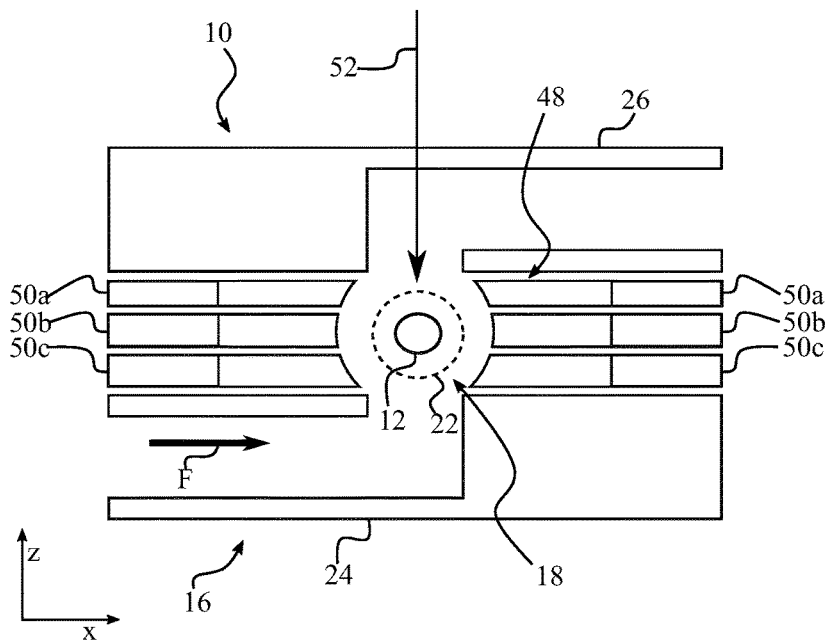
FIG. 10C is a schematic illustration of an aggregating system for aggregating a three-dimensional cluster of particles according to another example.
Figure 10D:
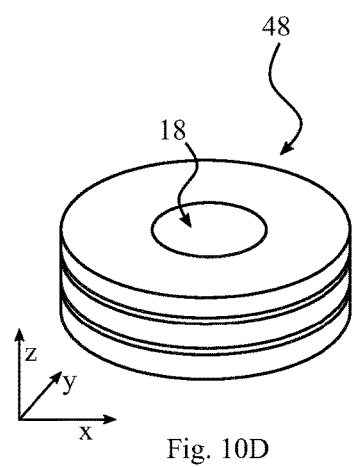
FIG. 10D is a perspective view of an acoustic lens employed in the example of FIG. 10C.

FIGS. 10A and 10C illustrate a side view of a system 10 featuring two embodiments of a three-dimensional acoustic lens 48 according to an example for aggregating a three-dimensional cluster 12 of particles 14 with similar spatial extension along three spatial dimensions. FIGS. 10B and 10D illustrate corresponding perspective views of the acoustic lens 48 of the examples of FIGS. 10A and 10C, respectively.

In FIGS. 10A and 10C, the inlet section 24 of the channel 16 is arranged below the retention section 18 formed by the acoustic lens 48, and the outlet section 26 is arranged above the retention section 18. In this vertical channel configuration, air bubbles interfering with optical transparency or acoustic wave resonance conditions can have a reduced probability for remaining in the retention section 18.

In FIGS. 10A and 10C, piezoelectric transducers 50 are operatively coupled to the acoustic lens 48 to introduce a retention force in the retention section 18 to thereby provide an aggregation region 22 for the cluster 12. The channel 16 should feature monitoring windows to allow monitoring the retention section 18 along the monitoring direction 52, the monitoring direction 52 being oriented substantially along the vertical z-direction of the channel 16. Preferably, the channel 16 allows monitoring of the inlet section 24 of the channel 16 upstream of the retention section 18 to monitor particles 14 in the fluid stream F which enter or are about to enter the retention section 18.

As can be seen from FIG. 10B, the acoustic lens 48 is ring shaped to delimit the retention section 18 along the lateral x- and y-directions of the channel 16 to provide lateral retention forces along the lateral x- and y-directions of the channel 16 similar to the acoustic cavities in the examples illustrated in the preceding figures. Additionally, the acoustic lens 48 is tapered along the vertical z-direction of the channel 16 to provide retention forces along the vertical z-direction. Thus, a three-dimensional aggregation region 22 can be defined using the acoustic lens 48.

The example according to FIG. 10C differs from the example of FIG. 10A in that the acoustic lens 48 comprises multiple segments for controlling a location and a shape of the retention forces for the aggregation region 22. Each segment is coupled to a separate piezoelectric transducer 50a, 50b, and 50c. In the system 10 according to FIG. 10C, the control device 38 can be configured to control the amplitude, frequency and phase between the piezoelectric transducers 50a, 50b, 50c to control a location of the cluster 12, a trapping potential distribution in the aggregation region 22 and/or an orientation of the cluster 12 by inducing a torque on the cluster 12 with the trapping potential 40. Thus, a three-dimensional cluster can be formed with compositional and structural control.

The description of the preferred embodiments and the Figures merely serve to illustrate the invention and the beneficial effects associated therewith, but should not be understood to imply any limitation. The scope of the invention is to be determined solely by the appended claims.

LIST OF REFERENCE SIGNS

10 system
12 cluster
14 particle
14a particles of the first type
14b particles of the second type
14m monitored particle
16 channel
18 retention section
20 retention mechanism
20a acoustic transducer
20b second acoustic transducer
22 aggregation region
24 inlet section
26 outlet section
28 first stream
30 supply of particles
32 fluid guiding section
34 fluid control mechanism
36 monitoring device
38 control device
40 trapping potential
42a first inlet
42b second inlet
42c third inlet
44 matrix material
46 large object
48 acoustic lens
50, 50a-c piezoelectric transducer
52 monitoring direction
F fluid stream

The invention claimed is:

1. A method for aggregating a cluster of particles having a target cluster constitution in a channel, the method comprising:
    establishing a fluid stream through said channel, said channel comprising a retention section, said fluid stream comprising a fluid carrier medium and particles of at least one type;
    controlling a supply of said particles of at least one type into the fluid stream;
    operating a retention mechanism to aggregate at least part of said particles in an aggregation region within said retention section, to thereby form said cluster of particles, wherein operating the retention mechanism comprises generating an acoustic field in the retention section using an acoustic wave generator of the retention mechanism;

monitoring, while operating said retention mechanism, the particles in at least part of said channel for obtaining a monitoring signal associated with the cluster and the particles moving in the fluid stream;
determining a current cluster constitution of said cluster from the monitoring signal;
comparing said current cluster constitution with said target cluster constitution; and
controlling at least one of said particle retention mechanism or said supply of said particles of at least one type, such that said current cluster constitution of said cluster dynamically approaches said target cluster constitution.

2. The method of claim 1, wherein the cluster constitution comprises information on at least one of: a size of the cluster, a composition of the cluster, a structure of the cluster, a shape of the cluster and an orientation of the cluster.

3. The method of claim 1, wherein the particles of at least one type are cells of at least one type or are formed by cells of at least one type and the cluster relates to a cluster of cells.

4. The method of claim 1, wherein operating the retention mechanism comprises generating an acoustic standing wave in the retention section, the standing wave having a pressure node or a pressure anti-node in the aggregation region.

5. The method of claim 1, wherein controlling said retention mechanism comprises adjusting a retention strength of the retention mechanism based on a size of the cluster determined from the monitoring signal.

6. The method of claim 1, wherein controlling said supply of said particles of at least one type comprises adjusting the concentration of said particles of at least one type in said fluid stream based on the current cluster constitution determined from the monitoring signal.

7. The method of claim 1, wherein said particles of at least one type comprise a first type of particles and a second type of particles, wherein the method further comprises:
controlling a supply of the first type of particles and of the second type of particles into the fluid stream, such that said current cluster constitution approaches said target cluster constitution, wherein said target cluster constitution comprises one or both of a target composition and a target structure.

8. The method of claim 1, wherein said monitoring signal represents at least one or both of a position and a velocity of one or more particles of said particles of at least one type.

9. The method of claim 1, wherein said monitoring signal is a microscope image or a series of microscope images of said particles arranged in said cluster.

10. The method of claim 1, wherein the cluster constitution comprises a number of particles in the cluster and wherein the number of particles is determined from at least one of a tracking history of a plurality of said particles of at least one type in said channel and from the size of the cluster in the retention section.

11. The method of claim 1, the method further comprising:
determining, from said monitoring signal, whether one or more particles of at least one type move into or are about to move into said retention section, and
controlling said retention mechanism, based on said current cluster constitution, for selectively directing said one or more particles to said cluster or for avoiding that said one or more particles reach said cluster.

12. An aggregating system for aggregating a cluster of particles having a target cluster constitution in a channel, the aggregating system comprising:
a fluid guiding section comprising said channel, said channel comprising a retention section,
a fluid control mechanism configured to
establish a fluid stream through said channel, said fluid stream comprising a fluid carrier medium and particles of at least one type; and
control a supply of said particles of at least one type into the fluid stream;
a retention mechanism associated with said channel and configured to aggregate at least part of said particles in an aggregation region within said retention section of said channel, to thereby form said cluster of particles, wherein the retention mechanism comprises an acoustic wave generator operatively coupled with the retention section to generate an acoustic field in the retention section;
a monitoring device configured for monitoring the particles in at least part of said channel to provide a monitoring signal associated with one or both of the cluster and the particles moving in the fluid stream; and
a control device configured to
operate said retention mechanism and said fluid control mechanism;
receive a monitoring signal from the monitoring device while operating said retention mechanism;
determine a current cluster constitution of said cluster from the monitoring signal;
compare said current cluster constitution with said target cluster constitution; and
control at least one of said retention mechanism and said supply of said particles of at least one type, such that said current cluster constitution of said cluster dynamically approaches said target cluster constitution.

13. The system of claim 12, wherein the acoustic wave generator is configured to generate a standing wave having a pressure node or a pressure anti-node in the aggregation region.

14. The system of claim 12, wherein said control device is configured to adjust a retention strength of the retention mechanism based on a size of the cluster determined from the monitoring signal.

15. The system of claim 12, wherein the control device is configured to control said supply of said particles of at least one type by adjusting the concentration of said particles of at least one type in said fluid stream (F) based on the current cluster constitution determined from the monitoring signal.

16. The system of claim 12, wherein said monitoring signal is an optical signal, wherein said monitoring device comprises a camera and a microscope and is configured to record a microscope image or a series of microscope images of said particles moving in the fluid stream.

17. The system of claim 12, wherein the control device is configured to:
determine, from said monitoring signal, whether one or more particles of at least one type move into or are about to move into said retention section, and
control said retention mechanism based on said current cluster constitution, for selectively directing said one or more particles to said cluster or for avoiding that said one or more particles reach said cluster.

18. The system of claim 12, wherein the cluster constitution comprises a number of particles in the cluster and wherein the control device is configured for determining the number of particles from one or both of a tracking history of a plurality of said particles of at least one type in said channel and the size of the cluster in the retention section.

19. The system of claim 12, wherein said particles of at least one type comprise a first type of particles and a second type of particles, wherein the control device is further configured to:
control a supply of the first type of particles and of the second type of particles into the fluid stream, such that said current cluster constitution approaches said target cluster constitution wherein said target cluster constitution comprises one or both of a target composition and a target structure.

20. A non-transitory computer-readable medium storing computer readable instructions that, when executed by a processor, cause the processor to control an aggregation system for aggregating a cluster of particles in a channel having a target cluster constitution by implementing a method with the steps of:
controlling a supply of said particles of at least one type into a fluid stream in said channel, said channel comprising a retention section;
operating a retention mechanism to aggregate at least part of said particles in an aggregation region within said retention section, to thereby form said cluster of particles, wherein operating the retention mechanism comprises generating an acoustic field in the retention section using an acoustic wave generator of the retention mechanism;
monitoring, while operating said retention mechanism, the particles in at least part of said channel for obtaining a monitoring signal associated with one or both of the cluster and the particles moving in the fluid stream;
determining a current cluster constitution of said cluster from the monitoring signal;
comparing said current cluster constitution with said target cluster constitution; and
controlling at least one of said retention mechanism or said supply of said particles of at least one type, such that said current cluster constitution of said cluster dynamically approaches said target cluster constitution.

* * * * *